United States Patent
Perez, III et al.

(10) Patent No.: US 9,775,676 B2
(45) Date of Patent: Oct. 3, 2017

(54) STEERABLE SURGICAL DEVICE WITH JOYSTICK

(71) Applicant: ARTHREX, INC., Naples, FL (US)

(72) Inventors: Arley Perez, III, Bonita Springs, FL (US); Mark Allan Wise, Bonita Springs, FL (US)

(73) Assignee: ARTHREX, INC., Naples, FL (US)

( * ) Notice: Subject to any disclaimer, the term of this patent is extended or adjusted under 35 U.S.C. 154(b) by 177 days.

(21) Appl. No.: 14/595,477

(22) Filed: Jan. 13, 2015

(65) Prior Publication Data

US 2015/0196364 A1    Jul. 16, 2015

Related U.S. Application Data

(60) Provisional application No. 61/926,489, filed on Jan. 13, 2014.

(51) Int. Cl.
| | |
|---|---|
| *F16H 21/44* | (2006.01) |
| *A61B 19/00* | (2006.01) |
| *A61B 17/29* | (2006.01) |
| *A61B 17/00* | (2006.01) |
| *A61B 18/14* | (2006.01) |
| *A61B 18/00* | (2006.01) |

(52) U.S. Cl.
CPC .......... *A61B 19/22* (2013.01); *A61B 17/2909* (2013.01); *A61B 18/14* (2013.01); *A61B 2017/00327* (2013.01); *A61B 2017/2927* (2013.01); *A61B 2018/0091* (2013.01)

(58) Field of Classification Search
CPC ...... A61B 19/22; A61B 17/2909; A61B 18/14
See application file for complete search history.

(56) References Cited

U.S. PATENT DOCUMENTS

| | | | |
|---|---|---|---|
| 2007/0225562 A1* | 9/2007 | Spivey | A61B 17/068 600/121 |
| 2007/0250110 A1* | 10/2007 | Lu | A61B 17/2909 606/205 |
| 2009/0312605 A1* | 12/2009 | Hallbeck | A61B 17/29 600/131 |
| 2012/0150155 A1* | 6/2012 | Kappel | A61B 17/2909 606/1 |
| 2014/0188091 A1* | 7/2014 | Vidal | A61B 17/2909 606/1 |
| 2014/0246477 A1* | 9/2014 | Koch, Jr. | A61B 17/068 227/180.1 |
| 2015/0150633 A1* | 6/2015 | Castro | A61B 17/29 606/130 |

FOREIGN PATENT DOCUMENTS

| | | |
|---|---|---|
| EP | 2147630 A2 | 1/2010 |
| WO | 2013116692 | 8/2013 |
| WO | WO 2013116692 A1 * | 8/2013 ......... A61B 1/00066 |

OTHER PUBLICATIONS

The International Preliminary Report on Patentability for PCT Application No. PCT/US2015/011121, dated Mar. 30, 2016.

* cited by examiner

*Primary Examiner* — Zakaria Elahmadi
(74) *Attorney, Agent, or Firm* — Carlson, Gaseky & Olds, P.C.

(57) ABSTRACT

A surgical device according to an exemplary aspect of this disclosure includes, among other things, a tool at a distal end of the surgical device, and a joystick including a ball. Movement of the joystick results in movement of the tool. The surgical device further includes a housing including a socket receiving the ball of the joystick.

17 Claims, 3 Drawing Sheets

STEERABLE SURGICAL DEVICE WITH JOYSTICK

BACKGROUND

Steerable surgical devices are used during surgical procedures, such as arthroscopic procedures, to allow access to anatomy that is otherwise inaccessible via rigid surgical instruments. One such device is Arthrex's Nav-X™. The Nav-X™, for example, includes a moveable hand piece, a rigid shaft extending from the hand piece, and an articulating end supporting a tool at a distal end of the device. During use, a surgeon positions the tool by moving the hand piece, and by using his hand or a patient's soft tissue as a fulcrum.

SUMMARY

A surgical device according to an exemplary aspect of this disclosure includes, among other things, a tool at a distal end of the surgical device, and a joystick including a ball. Movement of the joystick results in movement of the tool. The surgical device further includes a housing including a socket receiving the ball of the joystick.

In a further non-limiting embodiment of the foregoing surgical device, the surgical device includes a fulcrum assembly. The fulcrum assembly is arranged such that movement of the joystick in a first direction results in movement of the tool in the first direction.

In a further non-limiting embodiment of the foregoing surgical device, the fulcrum assembly includes an intermediate member within an internal cavity in a housing of the surgical device. The intermediate member is operably connected to the joystick.

In a further non-limiting embodiment of the foregoing surgical device, the intermediate member is operably connected to the joystick by a ball joint.

In a further non-limiting embodiment of the foregoing surgical device, at least one connecting wire is fixed to the intermediate member. The at least one connecting wire is configured to transmit mechanical force from movement of the intermediate member to the tool.

In a further non-limiting embodiment of the foregoing surgical device, the intermediate member includes a semispherical disk portion.

In a further non-limiting embodiment of the foregoing surgical device, the surgical device further includes a shaft connected to the housing. The shaft has a rigid portion and an articulating portion. The tool is connected to the articulating portion, and the at least one connecting wire extends through the shaft to the articulating portion.

In a further non-limiting embodiment of the foregoing surgical device, the fulcrum assembly includes a cup portion moveable relative to a fixed ball. The fixed ball is rigidly connected to the housing.

In a further non-limiting embodiment of the foregoing surgical device, the fixed ball includes a plurality of passageways, and the at least one connecting wire extends through the passageways in the fixed ball.

In a further non-limiting embodiment of the foregoing surgical device, the joystick is configured to pivot relative to a neutral axis to allow for a two dimensional input.

In a further non-limiting embodiment of the foregoing surgical device, the joystick is moveable in one of a forward direction and rearward direction while simultaneously moving in one of a leftward direction and rightward direction.

In a further non-limiting embodiment of the foregoing surgical device, the joystick includes an input surface connected to the ball of the joystick by a stick. The stick and input surface project through an orifice in the housing.

In a further non-limiting embodiment of the foregoing surgical device, the surgical device is electrically connected to a control unit to provide power to the tool.

In a further non-limiting embodiment of the foregoing surgical device, the surgical device includes a resilient member configured to urge the joystick to a neutral position.

A method according to an exemplary aspect of this disclosure includes, among other things, adjusting a position of a tool of a surgical device by moving a joystick.

In a further non-limiting embodiment of the foregoing method, movement of the joystick away from a neutral axis in a rearward direction results in a downward movement of the tool.

In a further non-limiting embodiment of the foregoing method, rearward movement of the joystick in the rearward direction results in an upward movement of a ball joint between the joystick and an intermediate member.

In a further non-limiting embodiment of the foregoing method, upward movement of the ball joint results in a forward rotation of the intermediate member.

In a further non-limiting embodiment of the foregoing method, the forward rotation of the cup portion results in mechanical forces being transmitted to the tool.

In a further non-limiting embodiment of the foregoing method, the position of the tool is adjusted by moving the joystick in one of a forward direction and rearward direction while simultaneously moving the joystick in one of a leftward direction and rightward direction.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

BRIEF DESCRIPTION OF THE DRAWINGS

The drawings can be briefly described as follows.

DETAILED DESCRIPTION

Figure 1:
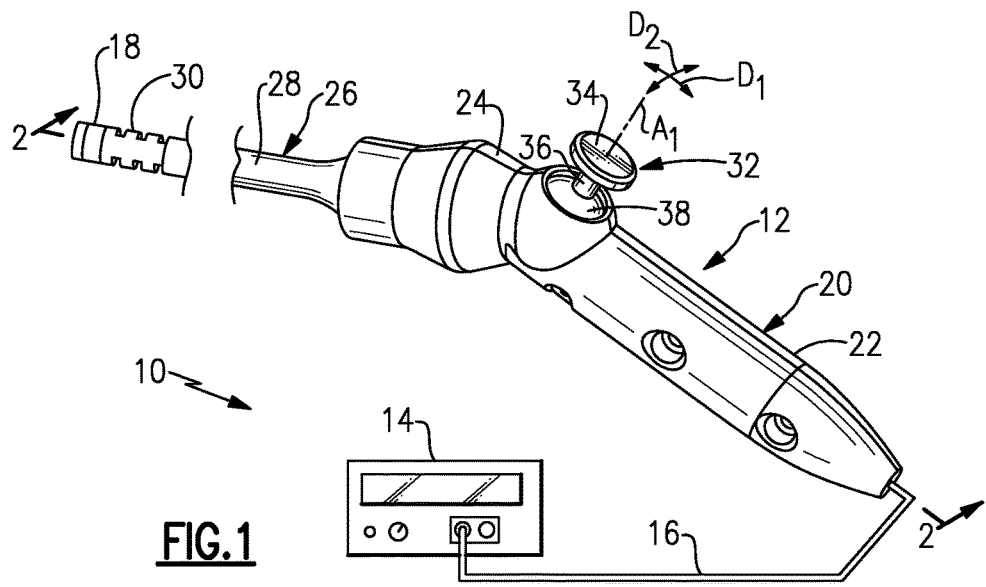
FIG. 1 illustrates an example surgical device and control system.

FIG. 1 illustrates a system 10 including a surgical device 12. In this example, the surgical device 12 is electrically connected to a control unit 14, which regulates the operation of the surgical device 12. It should be understood that the control unit 14 may include features generally known to be provided in control units, such as a processor, memory, and storage.

In this example, the control unit 14 is configured to provide power to the surgical device 12 by way of a conducting wire 16. The conducting wire 16 may be connected to a motor within the surgical device 12, or may be routed within the surgical device 12 to a tool 18 provided at a distal end of the surgical device 12. One example tool 18 is an ablation device.

Other tools that do not require power come within the scope of this disclosure. In these examples, the control unit 14 may not be necessary for operating of the surgical device 12. Example tools that do not require power include clamping devices, such as jaws. While not illustrated, a connecting wire may be routed from a moveable finger ring (i.e., a trigger) to the tool 18 to allow a surgeon to manipulate the jaws.

The example surgical device 12 includes a housing 20 providing a hand grip portion 22 and a joystick support portion 24. A shaft 26 projects from the joystick support portion 24, and extends between the joystick support portion 24 and the tool 18. In this example, the shaft includes a rigid portion 28 proximal to the housing 20 and an articulating portion 30 at a distal end of the rigid portion 28. As will be explained below, the articulating portion 30 supports the tool 18 and is moveable relative to the rigid portion 28.

A joystick 32 is supported by the housing 20, and at least partially projects outward from the housing 20 for manipulation by a user (e.g., a surgeon). The joystick 32 includes an input surface 34, a stick 36, and a ball 38. Details of the joystick 32 are illustrated in FIG. 2, which is a sectional view taken along line 2-2 in FIG. 1.

Figure 2:
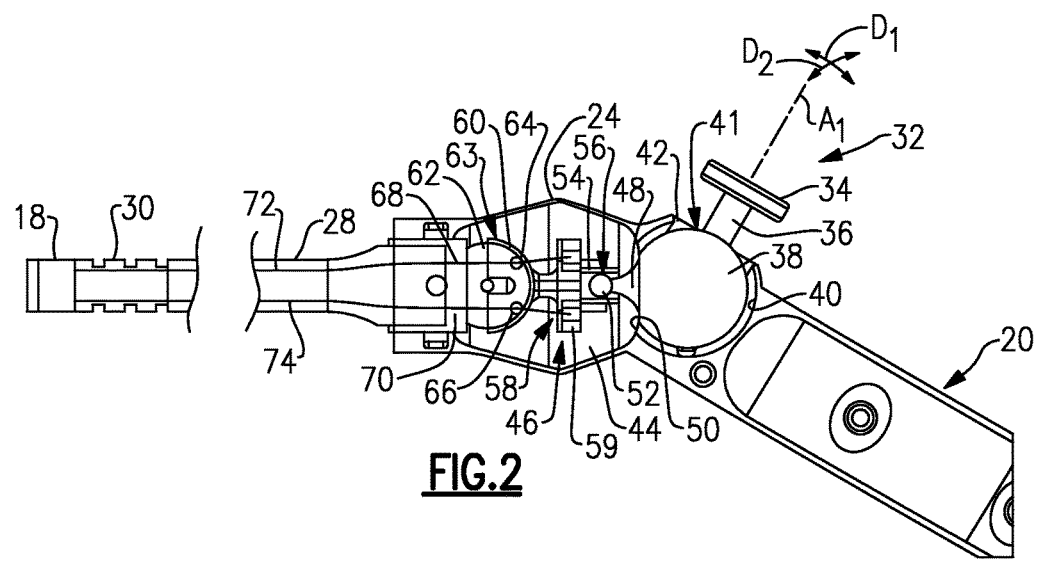
FIG. 2 is a cross-sectional view of the surgical device of FIG. 1, taken along line 2-2 from FIG. 1, and illustrates the joystick in a neutral, or center, position.

Referring to FIG. 2, the housing 20 includes a socket 40 receiving the ball 38 of the joystick 32. The ball 38 and socket 40 provide a first ball joint 41, which allows for two dimensional movement of the joystick 32 (discussed in more detail below). The input surface 34 and stick 36 project through an orifice 42 in the housing 20. Movement of the joystick 32 is restricted by the portion of the housing 20 that provides the perimeter of the orifice 42.

In FIG. 2, the joystick 32 is illustrated in a neutral, or center, position, such that the stick 36 extends along a neutral axis $A_1$. In some examples, the joystick 32 may be urged toward the neutral axis $A_1$ by way of a spring or other resilient member. The joystick 32 is moveable, and is configured to pivot relative to the neutral axis $A_1$. In particular, the joystick 32 in this example allows for a two dimensional input. That is, the joystick 32 can be pivoted off the axis $A_1$ in forward and rearward directions, illustrated at $D_1$, in leftward and rightward directions, illustrated at $D_2$, and in combinations of the directions $D_1$ and $D_2$. That is, the joystick is moveable in one of the forward and rearward directions $D_1$ while simultaneously moving in one of the leftward and rightward directions $D_2$. As will be explained in detail below, movement of the joystick 32 results in a corresponding movement of the tool 18.

The housing 20 further includes an internal cavity 44 that encloses a fulcrum assembly 46. In this example, the ball 38 of the joystick includes a projection 48 extending from the ball 38, and through an orifice 50 between the ball 38 and the internal cavity 44. The projection 48 includes a ball 52 at a terminal end. The ball 52 in this example is received in a socket 54. The ball 52 and the socket 54 provide a second ball joint 56 between the ball 38 and an intermediate member 58.

The intermediate member 58 is configured to move within the internal cavity 44. In this example, the intermediate member 58 includes a disk 59 within the internal cavity 44. Opposite the socket 54, the intermediate member 58 includes a cup portion 60 provided over a fixed ball 62, which is rigidly connected to the housing 20. The cup portion 60 and the fixed ball 62 provide a third ball joint 63. The cup portion 60 includes a plurality of orifices 64, 66, and the fixed ball 62 includes passageways 68, 70, for routing connecting wires 72, 74 from the intermediate member 58 to the articulating portion 30, via the shaft 26 (which includes a bore for routing the connecting wires 72, 74). In this example, the ball joint 63 acts as a fulcrum, or pivot point, between the input from the joystick 32 and the connecting wires 72, 74.

The connecting wires 72, 74 may each be provided by a single, individual wire that is fixed to the disk 59 at one end, and the articulating portion 30 at the other end. Alternatively, the connecting wires 72, 74 can be connected to the cup portion 60. The wires 72, 74 are relatively rigid along their length, but are configured to bend. In this way, the connecting wires 72, 74 are configured to transmit mechanical force from the movement of the disk 59 to the articulating portion 30, which results in movement of the tool 18. Alternatively, the connecting wires 72, 74 can be connected to the tool 18 directly. While only two connecting wires 72, 74 are illustrated in FIG. 2 (because FIG. 2 is a cross-sectional view), it should be understood that the illustrated example would include four connecting wires. This disclosure extends to devices that include a different number of connecting wires, however.

Alternatively, the connecting wires 72, 74 can be provided by a single piece of wire that has been looped over the orifices 64, 66. In this example, the wire would still be fixed to the cup portion adjacent the orifices 64, 66, with its ends fixed to the articulating portion 30, such that the movement of the disk 59 will be transmitted to the tool 18.

Figure 3:
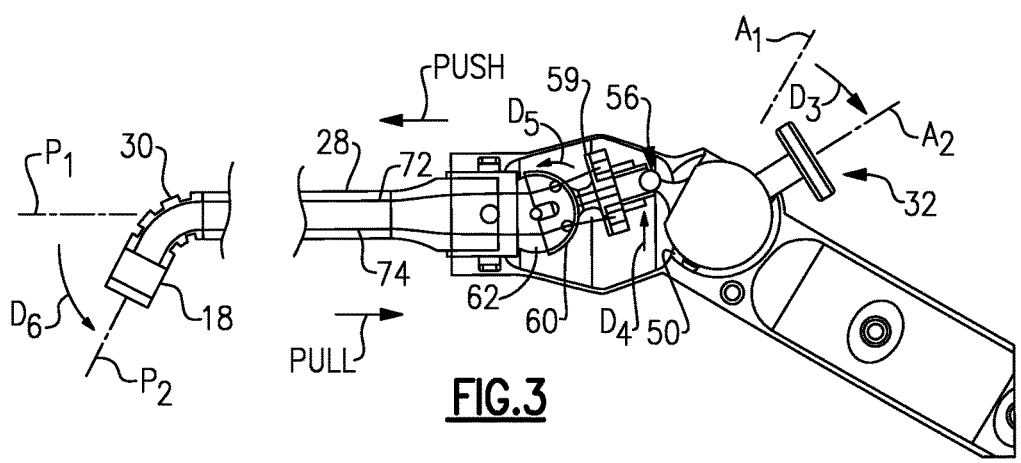
FIG. 3 is another cross-sectional view of the surgical device of FIG. 1, and illustrates an example movement of the joystick.

FIG. 3 illustrates an example movement of the joystick 32. In FIG. 3, the joystick 32 has been moved in a rearward direction $D_3$, off the neutral axis $A_1$, to second position defined about a second axis $A_2$. Rearward movement of the joystick 32 results in an upward movement, relative to FIG. 3, of the ball joint 56 in the direction $D_4$. Movement of the ball joint 56 in the direction $D_4$ causes forward rotation of the disk 59 in the direction $D_5$. This rotation of the disk 59 pulls the lower connecting wire 74 (see the term "pull" in FIG. 3), and pushes the upper connecting wire 72 (see the term "push" in FIG. 3). The connecting wires 72, 74 essentially bend the articulating portion 30 in a downward direction $D_6$ from an initial, neutral position $P_1$, to a second position $P_2$.

Again, as illustrated in FIG. 3, movement of the joystick 32 in the rearward direction $D_3$ results in movement of the tool 18 in the downward direction $D_6$. While not illustrated, one would understand that movement of the joystick 32 in a forward direction (relative to a user's perspective) would result in upward movement of the tool 18, leftward movement of the joystick 32 would result in leftward movement of the tool 18, and so on. In other words, the direction of movement of the joystick directly corresponds to the direction of movement of the tool 18. This disclosure thus provides intuitive steering of the tool 18 without requiring the use of an external fulcrum, such as a patient's soft tissue or an operator's (e.g., a surgeon's) hand.

While a particular fulcrum assembly 46 has been illustrated, it should be understood that other types of fulcrums may be used herein. For instance, the fulcrum assembly 46 in this example includes a plurality of ball joints. Other types of joints come within the scope of this disclosure.

Figure 4:
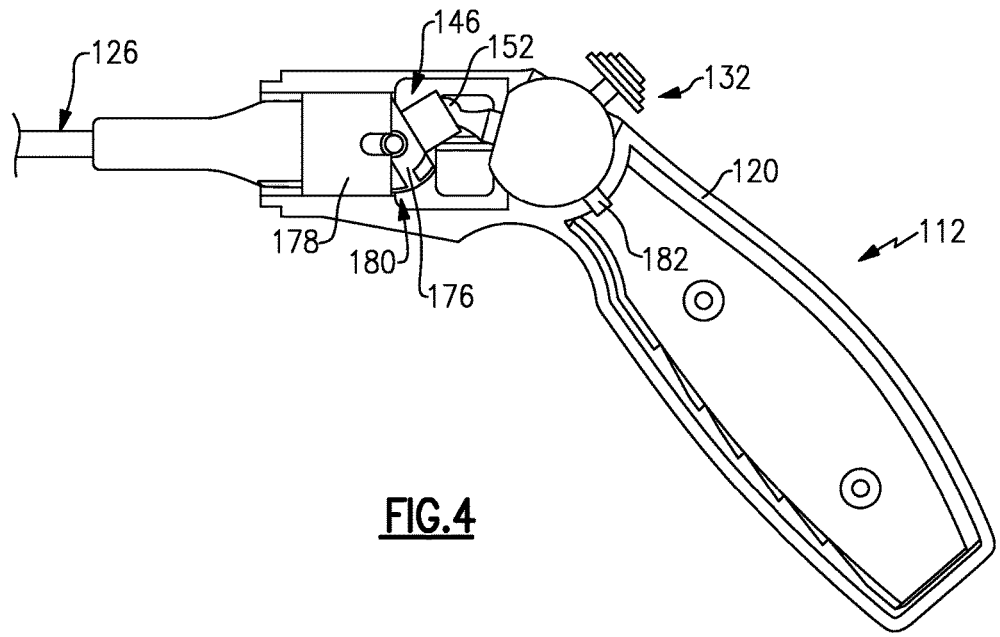
FIG. 4 is a cross-sectional view of another example surgical device.
Figure 5:
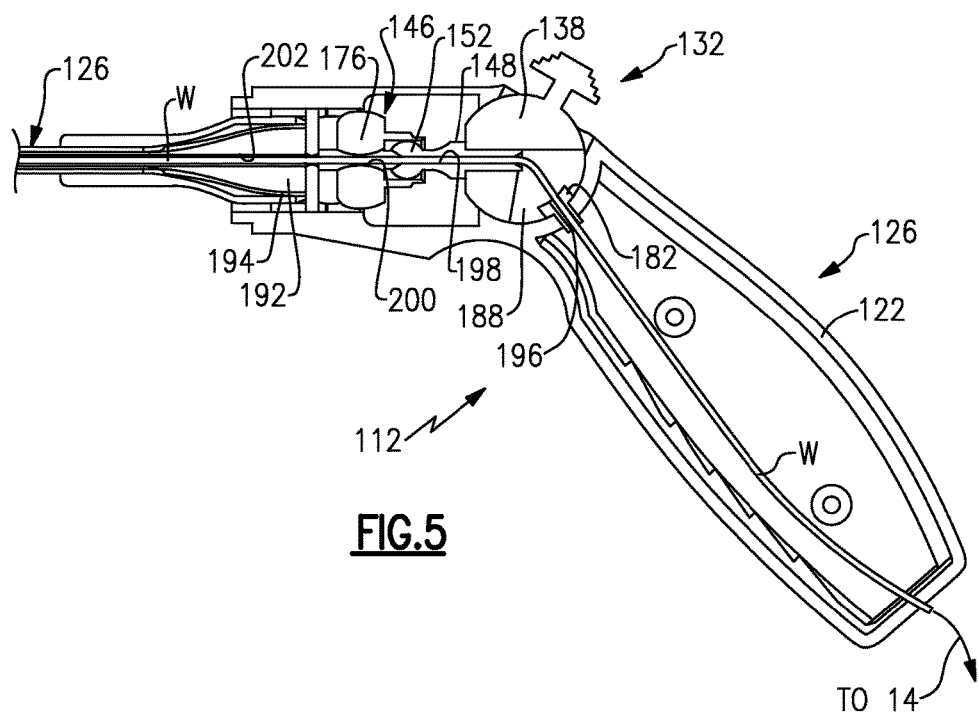
FIG. 5 is another cross-sectional view of the surgical device of FIG. 4.
Figure 6:
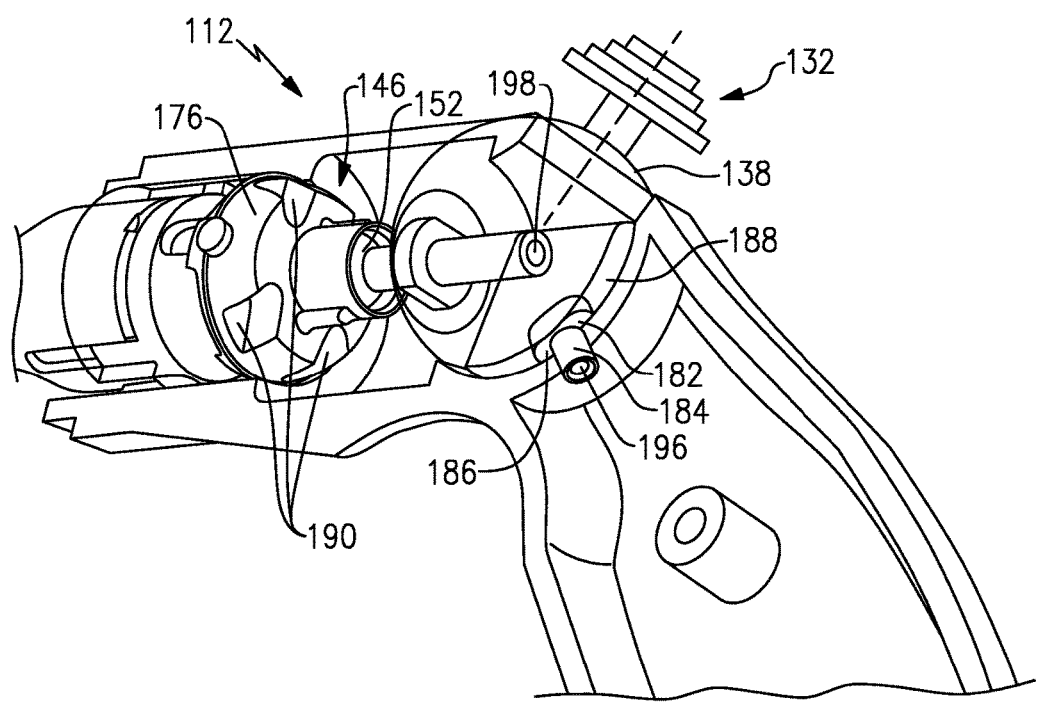
FIG. 6 is a further cross-sectional view of the surgical device of FIG. 4.

FIGS. 4-6 illustrate another example 112 surgical device according to this disclosure. To the extent not otherwise described or shown, the embodiment of FIGS. 4-6 corresponds to that of FIGS. 1-3, with like parts having reference numerals preappended with a "1."

With reference to FIG. 4, the surgical device 112 includes a fulcrum assembly 146 connected to the ball 152 of the joystick 132. The fulcrum assembly 146 is similar in function to the fulcrum assembly 46. However, instead of an intermediate portion including a disk 59 and a cup portion 60, the intermediate portion of the fulcrum assembly 146 is provided by a semi-spherical disk portion 176. The semi-spherical disk portion 176 is moveable within a fixed socket member 178, which is rigidly attached to the housing 120. The semi-spherical disk portion 176 and the fixed socket member 178 together provide a ball joint 180 that provides motion similar to the ball joint 63.

As mentioned above, the joystick may be urged toward a neutral axis by way of a spring or other resilient member. One example resilient member 182 is provided in the surgical device 112. Perhaps best seen in FIG. 6, the resilient member 182 includes a socket attachment portion 184, which is fixed to a socket surrounding the ball 138, and a ball engagement portion 186. The ball engagement portion 186 is received in a groove 188 in the ball 138. The ball engagement portion 186 is sized to fit snugly within the groove 188 in this example. As the ball 138 moves away from the neutral position, the resilient member 182 is configured to urge the joystick 132 toward the neutral position. The resilient member 182 may be made of any type of resilient material, such as rubber.

While not shown in FIGS. 4-6, the surgical device 112 includes connecting wires, like those of the example of FIGS. 1-3, between the semi-spherical disk portion 176 and the tool. In this example, the semi-spherical disk portion 176 includes four attachment sites 190 for connecting wires. The connecting wires, as in the prior embodiment, are routed through the shaft 126 to adjust the position of a tool.

Further, as seen in FIG. 5, the surgical device 112 includes a cable expander 192 between the semi-spherical disk portion 176 and the shaft 126. The connecting wires are routed around an outer diameter 194 of the cable expander 192 to space the connecting wires further apart from one another than at the semi-spherical disk portion 176.

Routing the connecting wires around the outer diameter 194 of the cable expander 192 has the advantage of exaggerating the motion of the joystick 132 at the tool. In one example, the cable expander 192 separates the connecting wires by a factor of three relative to the spacing at the semi-spherical disk portion 176. That is, the connecting wires are three times further apart at the cable expander 192. In that example, 30° of motion of the joystick 132 would result in 90° of motion of the tool. This feature reduces the amount of effort required from the user (e.g., a surgeon) to adjust the position of the tool.

As mentioned above, the tool 18 may be a powered tool. In order to provide electrical power to the tool, the components of the surgical device includes orifices that act as a conduit for routing an electrically conductive wire from a power source, such as the control unit 14, to the tool.

With reference to FIG. 5, the surgical device 112 provides one example conduit for an electrically conductive wire W. In the example, the wire W enters the housing 120 at the hand grip portion 122 and is directed through an orifice 196 in the resilient member 182. The wire W then passes through the groove 188 in the ball 138, and through another orifice 198 in the projection 148 of the ball 138. Next, the wire W passes through orifices 200 and 202 in the semi-spherical disk portion 176 and the cable expander 192, respectively. Finally, the wire W passes through the shaft 126 and to the tool. This arrangement prevents interference between the wire W and the moving components of the surgical device 112 (such as the ball 138 and the semi-spherical disk portion 176). Again, this is only one wire-routing arrangement. Other types of arrangements come within the scope of this disclosure.

It should be understood that terms such as "forward," "rearward," "rightward," "leftward," "distal," and "proximal" have been used herein for purposes of explanation, and should not be considered otherwise limiting. Terms such as "generally," "substantially," and "about" are not intended to be boundaryless terms, and should be interpreted consistent with the way one skilled in the art would interpret the term.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

What is claimed is:

1. A surgical device, comprising:
   a tool at a distal end of the surgical device;
   a joystick including a ball, wherein movement of the joystick results in movement of the tool;
   a housing including a socket receiving the ball of the joystick; and
   a fulcrum assembly, the fulcrum assembly arranged such that movement of the joystick in a first direction, relative to a perspective of a user of the surgical device, results in movement of the tool in the first direction relative to the perspective of the user of the surgical device, wherein the fulcrum assembly includes an intermediate member within an internal cavity in a housing of the surgical device, and wherein the intermediate member is operably connected to the joystick, wherein at least one connecting wire is fixed to the intermediate member, the at least one connecting wire configured to transmit mechanical force from movement of the intermediate member to the tool, and wherein the fulcrum assembly includes a cup portion moveable relative to a fixed ball, the fixed ball rigidly connected to the housing.

2. The surgical device as recited in claim 1, wherein the intermediate member is operably connected to the joystick by a ball joint.

3. The surgical device as recited in claim 1, wherein the intermediate member includes a semi-spherical disk portion.

4. The surgical device as recited in claim 1, further comprising a shaft connected to the housing, the shaft having a rigid portion and an articulating portion, wherein the tool is connected to the articulating portion, and wherein the at least one connecting wire extends through the shaft to the articulating portion.

5. The surgical device as recited in claim 1, wherein the fixed ball includes a plurality of passageways, the at least one connecting wire extending through the passageways in the fixed ball.

6. The surgical device as recited in claim 1, wherein the joystick is configured to pivot relative to a neutral axis to allow for a two dimensional input.

7. The surgical device as recited in claim 6, wherein the joystick is moveable in one of a forward direction and rearward direction while simultaneously moving in one of a leftward direction and rightward direction.

8. The surgical device as recited in claim 1, wherein the joystick includes an input surface connected to the ball of the joystick by a stick, the stick and input surface projecting through an orifice in the housing.

9. The surgical device as recited in claim 1, wherein the surgical device is electrically connected to a control unit to provide power to the tool.

10. The surgical device as recited in claim 1, further comprising a resilient member configured to urge the joystick to a neutral position.

11. A method, comprising:
adjusting a position of a tool of a surgical device by moving a joystick, the surgical device including a fulcrum assembly, the fulcrum assembly arranged such that movement of the joystick in a first direction, relative to a perspective of a user of the surgical device, results in movement of the tool in the first direction relative to the perspective of the user of the surgical device, wherein the fulcrum assembly includes an intermediate member within an internal cavity in a housing of the surgical device, and wherein the intermediate member is operably connected to the joystick, wherein at least one connecting wire is fixed to the intermediate member, the at least one connecting wire configured to transmit mechanical force from movement of the intermediate member to the tool, and wherein the fulcrum assembly includes a cup portion moveable relative to a fixed ball, the fixed ball rigidly connected to the housing.

12. The method as recited in claim 11, wherein movement of the joystick away from a neutral axis in a rearward direction results in a downward movement of the tool.

13. The method as recited in claim 12, wherein rearward movement of the joystick results in an upward movement of a ball joint between the joystick and an intermediate member.

14. The method as recited in claim 13, wherein upward movement of the ball joint results in a forward rotation of the intermediate member.

15. The method as recited in claim 14, wherein the forward rotation of the intermediate member results in mechanical forces being transmitted to the tool.

16. The method as recited in claim 11, wherein the position of the tool is adjusted by moving the joystick in one of a forward direction and rearward direction while simultaneously moving the joystick in one of a leftward direction and rightward direction.

17. The surgical device as recited in claim 1, wherein the perspective of the user of the surgical device is a fixed location.

* * * * *